United States Patent [19]

Callaway

[11] Patent Number: 4,955,872

[45] Date of Patent: Sep. 11, 1990

[54] INTRAVENOUS NEEDLE AND HOLDER ASSEMBLY

[76] Inventor: James Callaway, 300 25th Ave. North, Nashville, Tenn. 37203

[21] Appl. No.: 314,789

[22] Filed: Feb. 24, 1989

Related U.S. Application Data

[63] Continuation-in-part of Ser. No. 62,584, Jun. 16, 1987, abandoned.

[51] Int. Cl.⁵ .......................................... B61M 5/158
[52] U.S. Cl. ..................................... 604/273; 604/272
[58] Field of Search ............... 604/273, 272, 240, 280, 604/264, 164; 128/754

[56] References Cited

U.S. PATENT DOCUMENTS

| | | |
|---|---|---|
| 1,453,309 | 5/1921 | Eberly . |
| 1,503,339 | 7/1924 | Webb . |
| 1,578,517 | 3/1926 | Heir . |
| 2,569,901 | 10/1951 | Richard . |
| 3,884,230 | 5/1975 | Wueff . |
| 3,949,746 | 4/1976 | Wallach . |
| 4,108,068 | 12/1979 | Jacobsen et al. . |
| 4,257,463 | 3/1981 | Bailey ................... 128/766 |
| 4,403,617 | 9/1983 | Tretinyak ............ 128/754 |
| 4,529,399 | 7/1985 | Groshong et al. ...... 604/53 |

Primary Examiner—Stephen C. Pellegrino
Attorney, Agent, or Firm—Fleit, Jacobson, Cohn, Price, Holman & Stern

[57] ABSTRACT

In an intravenous needle and needle holder assembly, the needle is attached to an inner case, through which intravenous fluid is supplied, by a length of flexible tubing. An outer case is provided which surrounds the tubing during insertion of the needle into a patient's vein, so as to rigidify the needle during such insertion. After insertion, the outer case can be removed from at least a part of the flexible tubing so that the tubing provides a flexible connection between the inner case and the needle useful during administration of intravenous fluid.

20 Claims, 2 Drawing Sheets

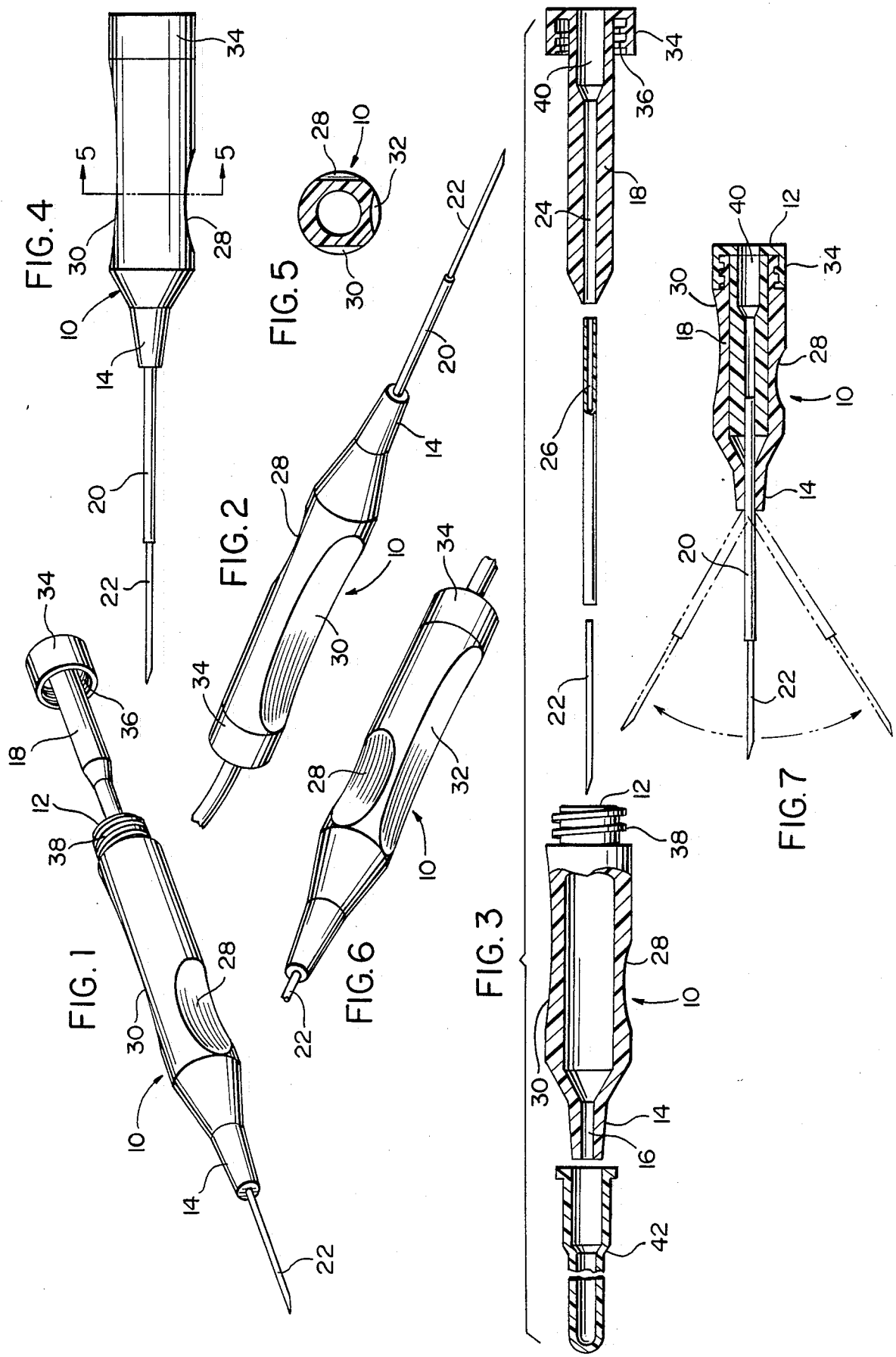

INTRAVENOUS NEEDLE AND HOLDER ASSEMBLY

CROSS-REFERENCE TO RELATED APPLICATION

This application is a continuation-in-part application of application Ser. No. 07/062,584 filed June 16, 1987, now abandoned.

FIELD OF THE INVENTION

This invention relates generally to the field of intravenous fluid administration, and more particularly to intravenous needle and needle holder assemblies which, inter alia, facilitate needle insertion and enhances user comfort.

BACKGROUND OF THE INVENTION

Intravenous fluids are being utilized with increasing frequency, and generally are administered through a conventional steel needle or an intravenous catheter. Steel needles are less irritating to veins than catheters but are difficult to immobilize if rigidly connected to a holder. The use of a syringe for insertion of a needle, necessitates disconnecting the needle and its associated attachments to the intravenous tubing, which frequently dislocates the needle. The use of catheters, on the other hand, is associated with a significant increase in the incidence of phlebitis.

SUMMARY OF THE INVENTION

It is an object of the invention to provide an intravenous needle and holder assembly which overcomes previously encountered difficulties with the insertion and immobilization of such needles.

Another object of the invention is to provide an intravenous needle and holder assembly which has different insertion and administration modes, so as to facilitate insertion and aid in immobilization of the needle.

In accordance with the invention, an intravenous needle and holder assembly includes a needle which is connected to an inner case by a length of flexible tubing, the inner case being adapted for connection to an intravenous fluid supply tube, and an outer case for surrounding and thereby rigidifying the flexible tubing relative to the inner case during insertion of the needle, the outer case being removable from at least a part of the tubing after insertion of the needle to expose said part of the tubing which thereby provides flexibility between the needle and the inner case during administration of a fluid therethrough.

In one form of the invention, the outer case has a forward end with a small needle-receiving bore formed therein, and an open back end, the inner case is receivable in the outer case with the needle projecting through said bore, the assembly has an insertion orientation wherein the needle projects only partially from said bore so as to provide a substantially rigidified junction with the outer case, and the assembly has an administration orientation wherein the outer case is withdrawn along the inner case to expose at least part of said length of flexible tubing from the forward end of the inner case and provide a substantially flexible junction between the needle and the outer case permitting movement of the outer case relative to the needle thereby facilitating immobilization of the outer case.

There may be a screw-thread connection between the inner and outer cases for securing these together in the administration orientation of the assembly, and the outer case may be contoured to facilitate handling and immobilization on a patient's arm. The back end of the inner case may be formed as a socket to receive a push-in fitting at the leading end of the intravenous tubing.

In another form of the invention, the outer case comprises two elongate trough-like sections which fit together around the flexible tubing during insertion of the needle and extend over a forward portion of the needle, thereby rigidifying the assembly for insertion of the needle. After insertion, the two halves of the outer case can be separated and removed thereby allowing the flexible tubing to provide a flexible junction between the inner case and the needle.

BRIEF DESCRIPTION OF THE DRAWINGS

FIG. 1 is a perspective view from one side of a first embodiment intravenous needle and holder assembly in an insertion orientation;

FIG. 2 is a perspective view from the other side of the assembly in an administration orientation;

FIG. 3 is an exploded sectional elevational view of the assembly;

FIG. 4 is a plan view of the assembly in the administration orientation;

FIG. 5 is a sectional view on line 5—5 of FIG. 4;

FIG. 6 is a perspective view from below of the assembly, in the administration orientation and part broken away;

FIG. 7 is a sectional plan view of the assembly in the administration orientation, showing how the needle can be moved relative to the outer case;

DESCRIPTION OF THE PREFERRED EMBODIMENT

Figure 8:
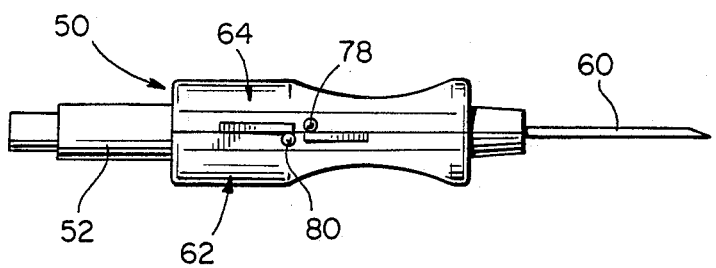
FIG. 8 is a plan view of a second embodiment intravenous needle and holder assembly in accordance with the invention.

A first embodiment intravenous needle and holder assembly as illustrated in FIGS. 1 through 7 comprises an elongate outer case 10, with an open back end 12 and a tubular front end 14 with a restricted bore 16, (FIG. 3), an elongate tubular inner case 18 which fits in the outer case, a length of flexible tubing 20 extending from a forward end of the inner case, and a conventional type of steel or other intravenous needle 22 at a forward end of the tubing. The inner case has a through-bore 24 communicating with a through-bore 26 in tubing 20, and another through-bore (not shown) in the needle. The inner and outer cases conveniently may be molded plastic, and the tubing 20 may be bonded or welded to the inner case and the needle in known manner.

The relative dimensions of the parts is such that needle 22 can be inserted into the outer case 10 from its back end, and pushed through bore 16 so that only a portion of the needle projects from the front of end 14 of the outer case, as shown in FIG. 1. This is the insertion orientation of the assembly, and it will be readily understood that in this orientation, there is a substantially rigidified junction between needle 22 and front end 14 of the outer case, substantially preventing any lateral displacement of the needle relative to the outer case and thereby stabilizing same to facilitate insertion of the needle into a patient's blood vessel. To further facilitate manipulation of the assembly, outer case 10 may have a thumb indentation 28 on one side and a longer finger indentation 30 on the other side.

Once the needle has been inserted in a patient's blood vessel, outer case 10 can be drawn backwardly along the inner case to an administration orientation of the assembly exposing tubing 20 from the forward end 14 of the outer case as shown, for example, in FIGS. 2, 4 and 7. This allows the outer case to pivot laterally relative to the needle about the tubing (see FIG. 7) thereby facilitating immobilization of the outer case by adhesive tape or the like on the patient's arm. The outer case may have a further elongate indentation or flat 32 on the bottom to aid in conforming to the contours of the arm and promote stabilization of the case on the patient.

It will further be noted that the back end of the inner case 18 is formed as a cap-like member 34 with internal threads 36 which can be threaded on complimentary external threads 38 on the outer case to lock the assembly in the administration orientation. Also, the back end of inner case 18 may be formed with a socket 40 to receive a press-in fitting of an intravenous tube. A removable needle cap 42 may also be provided.

Figure 9:
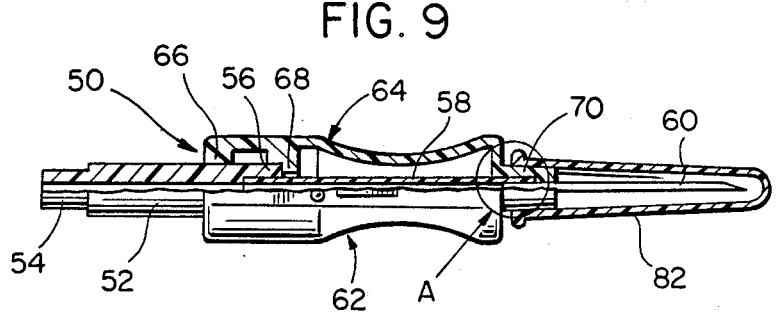
FIG. 9 is an enlarged sectional elevational view of the second embodiment assembly.
Figure 10:
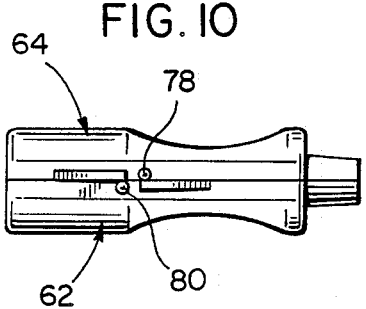
FIG. 10 is a plan view of the outer case of the second embodiment assembly.
Figure 11:
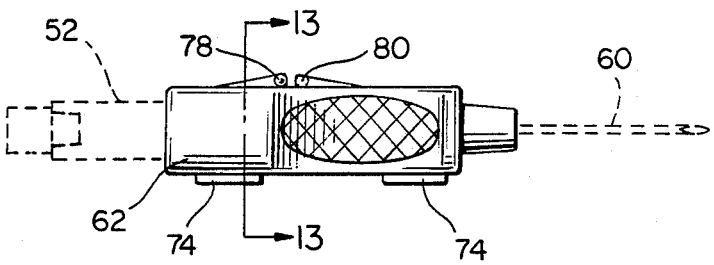
FIG. 11 is an elevational view of the outer case.
Figure 12:
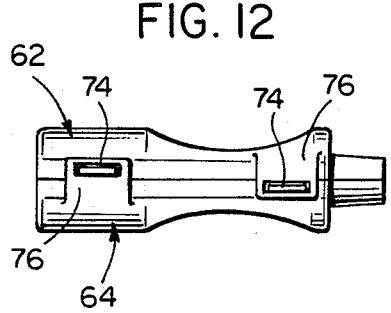
FIG. 12 is an underneath plan view of the outer case.
Figure 13:
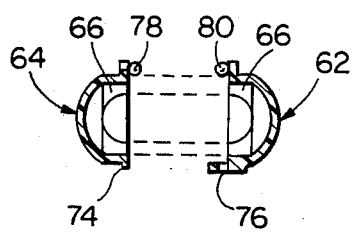
FIG. 13 is a sectional view on line 13—13 of FIG. 12 showing separation of the two parts of the outer case.
Figure 14:
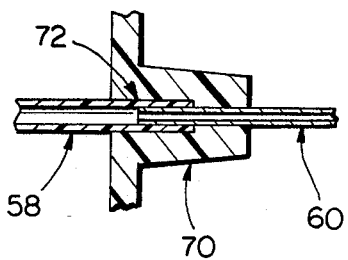
FIG. 14 is an enlarged view of the details shown circled by arrow A in FIG. 9.

The second embodiment needle assembly 50 shown in FIGS. 8-14 again has an inner case 52, which may be a plastic molding having a back end 54 adapted for connection to intravenous tubing. The front end 56 of the inner case is again connected via a length of flexible tubing 58 to a steel or like intravenous needle 60. An outer case in the second embodiment comprises two elongate, trough-like, fit-together halves 62 and 64 (conveniently plastic moldings) which, when the assembly is supplied to a user, are fitted together around the entire length of tubing 58 and extend over the back end portion of needle 60 so as to rigidify the connection between the needle and the inner case. As seen most clearly in FIGS. 9 and 14, the outer case is formed with internal bosses 66, 68 which grip the inner case and a forward boss 70 which grips the needle and the forward end of tubing 58. Further, adjacent boss 70 the outer case has an internal thrust bearing spike 72, (FIG. 14) which grips tubing 58 to preclude the tubing and needle from moving lengthwise in the outer case during needle insertion.

The two sections 62 and 64 of the outer case may fit together through hook-and-eye type attachments 74, 76 at the bottom of the respective sections and interengaging friction snaps 78, 80 on the tops of the respective sections. The needle may be provided with a protective cap 82 which is removed for use.

As noted above, the assembly may be supported with the outer case assembled on the inner case and needle so as to rigidify the needle for insertion. After insertion, the outer case may be removed by releasing the snaps 78, 80 and separating the sections 62 and 64. Accordingly, the needle is then provided with a flexible connection with the inner case 52 for administration of fluids as in the previous embodiment. The second embodiment may be considered more economical and somewhat simpler in construction and use than the first embodiment.

It is apparent that the invention accordingly provides an intravenous needle holder assembly which can be readily converted as between an insertion position wherein the needle is held substantially rigidly, and an administration position wherein a degree of flexibility is afforded between the needle and holder, to allow for some shifting of the holder, in use, without dislocating the needle or shifting in position of the needle with consequent alteration in the rate of intravenous fluid flow.

While only a preferred embodiment of the invention has been described herein in detail, the invention is not limited thereby and modifications can be made within the scope of the attached claims.

What is claimed is:

1. An intravenous needle and holder assembly having an outer case, an intravenous needle for receipt in the outer case with at least a part of the needle projecting from a forward end of the case, and adjustment means attached to a back end of the needle for selectively establishing an insertion orientation of the assembly having a substantially rigidified junction between the needle and the case effectively preventing lateral movement of the case, relative to the needle, and an administration orientation of the assembly having a flexible junction between the needle and the case allowing lateral movement of the case relative to the needle.

2. The invention as defined in claim 1 wherein the adjustment means includes a length of flexible tubing, the needle being movable along a bore in the forward end of the case between a first position establishing the insertion orientation of the assembly wherein only a part of the needle protrudes from the forward end of the case, and a second position establishing the administration orientation of the assembly wherein the entire needle and at least part of said flexible tubing protrudes from the forward end of the case.

3. The invention as defined in claim 2 further including an inner case attached to a back end of said tubing for receipt in the outer case and for connection to intravenous tubing.

4. The invention as defined in claim 3 including connector means between the inner case and outer case for releasably locking the assembly in the administration orientation.

5. The invention as defined in claim 4 wherein the connector means comprises a cap formation on the inner case, an internal thread on said cap formation and a corresponding external thread on the outer case.

6. The invention as defined in claim 2 including a socket in the inner case for receiving a press-in fitting on intravenous tubing.

7. The invention as defined in claim 1 including thumb and finger indentations on the outer case to facilitate insertion of the needle in a patient's blood vessel.

8. The invention as defined in claim 7 further including a flattened surface on the outer case to facilitate immobilization of the outer case on a patient's arm.

9. An intravenous needle and holder assembly including an outer case having a forward end with a small needle-receiving bore formed therein and an opened back end, an inner case for connection to intravenous tubing, the inner case having a forward end connection to an intravenous needle by a length of flexible tubing, the inner case being receivable in the outer case with the needle projecting through said bore, the assembly having an insertion orientation wherein the needle projects only partially from said bore so as to provide a substantially rigidified junction with the outer case, and the assembly having an administration orientation wherein the outer case is withdrawn along the inner case to expose at least part of said length of flexible tubing from the forward end of the outer case and provide substantially flexible movement of the outer case relative to the needle thereby facilitating immobilization of the outer case.

10. The invention as defined in claim 9 including a screw-threaded connection between the inner case and the outer case for securing the cases together in the administration orientation of the assembly.

11. The invention as defined in claim 9 wherein the outer case is contoured to facilitate handling and immobilization on a patient's arm.

12. The invention as defined in claim 9 including a socket formation at a back end of the inner case to receive a push-in fitting at the leading end of intravenous tubing.

13. An intravenous needle and holder assembly which includes a needle, an inner case having a through-bore, a back end for connection to a supply of intravenous fluid and a forward end, a length of flexible tubing connecting the forward end of the inner case to a back end of the needle, and an outer case for surrounding and thereby rigidifying the flexible tubing during insertion of the needle, the outer case being removable from at least a part of the tubing after insertion of the needle to expose said part of the tubing for providing flexibility between the needle and the inner case during administration of a fluid therethrough.

14. The assembly as defined in claim 13 wherein the outer case is configured to surround the entire length of said tubing as well as gripping a forward end portion of the inner case and a back end portion of the needle.

15. The assembly as defined in claim 14 wherein the outer case has means for entirely separating same from the flexible tubing.

16. The assembly as defined in claim 15 wherein the outer case comprises two interfitting elongate trough-like sections and said means for separating comprises detachable fastener means between the sections.

17. The assembly as defined in claim 16 wherein the fastener means comprises hook-and-eye type fastener means on one side of the outer case, and frictional-snap type fastener means on an opposite side of the outer case.

18. The assembly as defined in claim 14 wherein the outer case has as least one back end internal boss for gripping the inner case and a front end internal boss for gripping the needle.

19. The assembly as defined in claim 18 wherein the outer case includes an internal thrust means for engaging the flexible tubing and preventing lengthwise movement of the tubing and needle in the outer case during insertion of the needle.

20. The assembly as defined in claim 19 wherein the thrust means is located adjacent the front end boss.

* * * * *